United States Patent [19]

Hiura et al.

[11] Patent Number: 5,460,957
[45] Date of Patent: Oct. 24, 1995

[54] CALCIUM ALGINATE OLIGOSACCHARIDE AND METHOD FOR PRODUCING THE SAME FROM POTASSIUM OR SODIUM ALGINATE

[75] Inventors: Nozomi Hiura; Tomoaki Ooguri; Hiromi Nagayama; Tomohiro Takeda; Takamasa Tsuchida; Ryoichi Sato, all of Ibaraki, Japan

[73] Assignee: Maruha Corporation, Chiyoda, Japan

[21] Appl. No.: 45,235

[22] Filed: Apr. 1, 1993

[30] Foreign Application Priority Data

Apr. 28, 1992 [JP] Japan .................................. 4-110520
Feb. 17, 1993 [JP] Japan .................................. 5-028270

[51] Int. Cl.$^6$ .......................... C08B 37/04; C12P 19/04; C12P 19/12
[52] U.S. Cl. ............................ 435/100; 536/3; 536/123; 536/123.13; 435/101
[58] Field of Search ................ 514/54; 536/3, 536/123, 123.13; 435/100, 101

[56] References Cited

U.S. PATENT DOCUMENTS

| 4,804,536 | 2/1989 | Fukuda .................... 424/195.1 |
| 4,993,185 | 2/1991 | Adachi et al. ............... 47/58 |
| 5,139,945 | 8/1992 | Liu ........................... 435/232 |
| 5,141,927 | 8/1992 | Krotkiewski ................ 514/54 |
| 5,283,076 | 2/1994 | Kazuyuki et al. ............ 426/575 |

FOREIGN PATENT DOCUMENTS

| 0150574 | 8/1985 | European Pat. Off. . |
| 59-34853 | 2/1984 | Japan . |
| 63-088329 | 2/1988 | Japan . |
| 63-214192 | 9/1988 | Japan . |
| 63-290582 | 9/1988 | Japan . |
| 2-033507 | 12/1990 | Japan . |
| 2-303468 | 12/1990 | Japan . |
| 672896 | 5/1952 | United Kingdom . |

OTHER PUBLICATIONS

"Water–soluable degradation products of alginic acid", Chemical Abstracts, 90–73868, Mar. 1990, 131530j, Y. Kaneko et al.
"Medicine Contain Composition Soluable Contain Low Viscosity Alginate", Chemical Abstracts, 2–225422, Sep. 1990, Kimitsu Kagaku Kogy.
"Effects of Sodium–binding capacity of dietary fibers on blood pressure in spontaneously hypertensive rats", Chemical Abstracts, 72442n, 1993, By K. Tsuji et al.

Primary Examiner—Marian C. Knode
Assistant Examiner—Francisco C. Prats
Attorney, Agent, or Firm—Young & Thompson

[57] ABSTRACT

This invention provides alginate oligosaccharides comprising calcium alginate oligosaccharide, which is obtained by treating potassium alginate and/or sodium alginate with a polysaccharide-decomposing enzyme (alginate lyase) produced by a microorganism and substituting potassium ion or sodium ion in the potassium alginate oligosaccharide or sodium alginate oligosaccharide thus obtained with calcium ion, and potassium-enriched potassium alginate oligosaccharide, which is obtained by substituting sodium ion in said oligosaccharide with potassium ion, and a method for producing the same. The present invention further provides a food which contains the above-mentioned alginate oligosaccharide and exhibits an antihypertensive action.

4 Claims, 5 Drawing Sheets

(a)

(b)

(c)

(d)

mannuronic acid
or guluronic acid mannuronic acid guluronic acid

In the above structures (a) to (d), R represents H, Na, Ca or K.

5,460,957

CALCIUM ALGINATE OLIGOSACCHARIDE AND METHOD FOR PRODUCING THE SAME FROM POTASSIUM OR SODIUM ALGINATE

BACKGROUND OF THE INVENTION

1. Field of the Invention

This invention relates to an alginate oligosaccharide such as calcium alginate oligosaccharide or potassium alginate oligosaccharide, more particularly, an alginate oligosaccharide having an anti-hypertensive action and a method for producing the same.

The present invention further relates to an anti-hypertensive food containing the above-mentioned alginate oligosaccharide.

2. Description of the Prior Art

Seaweeds have been generally used as everyday foodstuffs and thought to be effective in maintaining the health and preventing hypertension and aging for a long time. It is known that brown algae such as sea tangle, from among the seaweeds, particularly contribute to the reduction of blood pressure thanks to the actions of alginic and amino acids contained therein.

However it is generally difficult in our daily diet to continuously take a large amount of seaweeds.

Therefore, it is desirable to make seaweeds easy to take by, for example, adding processed products of seaweeds to foods.

Alginic acid (potassium alginate or sodium alginate), which is a major intercellular mucopolysaccharide contained in brown algae, comprises D-mannuronic acid and L-guluronic acid as its major constituting molecules. It is considered that alginate oligosaccharides can be obtained by lowering the molecular weight of this alginic acid.

However, it is known that alginic acid is very hardly decomposable, since an aqueous solution of alginic acid is highly viscous and the alginic acid forms a metal salt together with, for example, calcium contained in said aqueous solution and thus sets to gel.

Regarding treatments of alginic acid, attempts have been made to decompose this substance by using an alginate lyase produced by a microorganism. There have been reported various examples of such a lyase on a laboratory level.

The oligosaccharides obtained by using the above-mentioned lyase include sodium alginate oligosaccharide and potassium alginate oligosaccharide. The potassium alginate oligosaccharide contains a large amount of sodium in addition to potassium, seemingly due to the purity of the potassium alginate of the polysaccharides employed as a starting material. On the other hand, there has been provided no report on the calcium alginate oligosaccharide. Further, there has been reported neither any physiological activity such as an antihypertensive action of these oligosaccharides nor any application of them to foods.

SUMMARY OF THE INVENTION

It is the first object of the present invention to provide an alginate oligosaccharide (calcium alginate oligosaccharide or potassium-enriched potassium alginate oligosaccharide), which is obtained from sodium alginate and/or potassium alginate and effective in maintaining the health by, for example, preventing hypertension, and a method for producing the same.

It is the second object of the present invention to provide an antihypertensive food which is effective in preventing hypertension.

In order to achieve the first object of the present invention, there is provided calcium alginate oligosaccharide characterized in that potassium ion or sodium ion in potassium alginate oligosaccharide or sodium alginate oligosaccharide, which is obtained by treating potassium alginate and/or sodium alginate with a polysaccharide-decomposing enzyme (alginate lyase) produced by a microorganism, is substituted by calcium ion.

The present invention further provides potassium alginate oligosaccharide characterized in that potassium ion or sodium ion in potassium alginate oligosaccharide or sodium alginate oligosaccharide, which is obtained by treating potassium alginate and/or sodium alginate with a polysaccharide-decomposing enzyme (alginate lyase) produced by a microorganism, is substituted by potassium ion to thereby elevate the ratio of the potassium ion content to the sodium ion content in said oligosaccharide (hereinafter referred to simply as to enrich with potassium ion).

In order to active the second object of the present invention, there is provided an antihypertensive food containing the above-mentioned alginate oligosaccharide such as calcium alginate oligosaccharide or potassium alginate oligosaccharide.

In order to achieve the above-mentioned objects, the present invention further provides a method for producing calcium alginate oligosaccharide characterized by treating potassium alginate and/or sodium alginate with a polysaccharide-decomposing enzyme (alginate lyase) produced by a microorganism, once deionizing the potassium alginate oligosaccharide and/or sodium alginate oligosaccharide thus obtained, treating the resulting product with a calcium hydroxide and then desalting and purifying the calcium alginate oligosaccharide thus obtained.

Furthermore, the present invention provides a method for producing potassium alginate oligosaccharide characterized by treating potassium alginate and/or sodium alginate with a polysaccharide-decomposing enzyme (alginate lyase) produced by a microorganism, once deionizing the potassium alginate oligosaccharide and/or sodium alginate oligosaccharide thus obtained, treating the resulting product with a potassium hydroxide and then desalting and purifying the potassium alginate oligosaccharide thus obtained.

As the microorganism to be used in the above-mentioned methods for producing alginate oligosaccharides, one belonging to the genus Alteromonas may be selected. The microorganism belonging to the genus Alteromonas is Alteromonas sp. No. 1786 strain.

BRIEF DESCRIPTION OF THE DRAWINGS

FIG. 4(a) is an elution pattern of sodium alginate oligosaccharide in HPLC, while

DETAILED DESCRIPTION OF THE INVENTION

Figure 1:
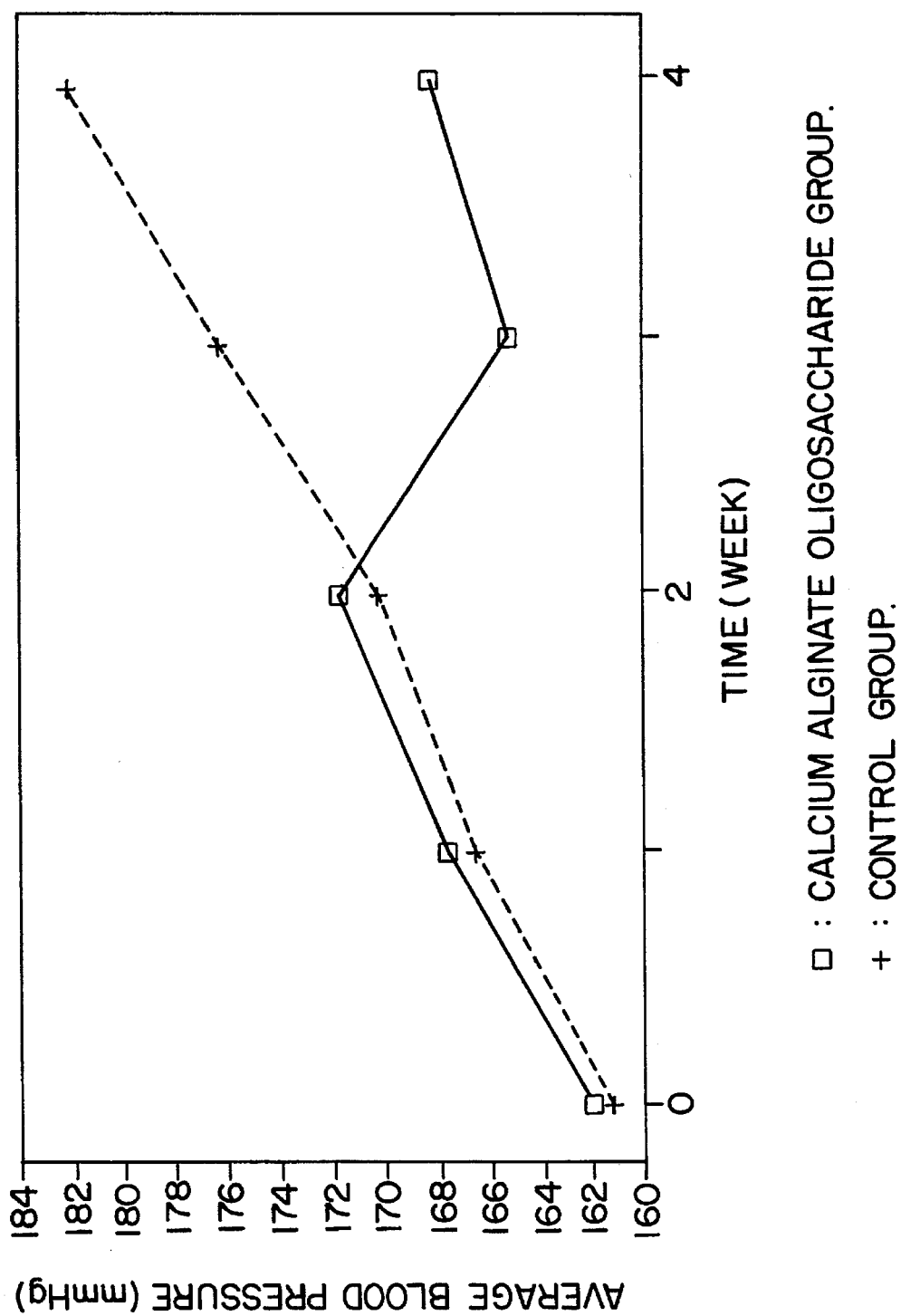
FIG. 1 is a graph showing the antihypertensive action of the calcium alginate oligosaccharide according to the present invention in an antihypertensive action test described in Example 5 as will be given hereinafter wherein spontaneous hypertensive rats (SHR) were used.

Now, the calcium alginate oligosaccharide or potassium-enriched potassium alginate oligosaccharide (hereinafter referred to collectively as alginate oligosaccharides) of the present invention will be described in greater detail based on the method for the production thereof according to the present invention.

As examples of the potassium alginate or sodium alginate to be used as the starting material for producing the alginate oligosaccharides of the present invention, potassium alginate and sodium alginate originating in sea tangle and wakeme (*Undaria pinnatifida*) may be cited.

The polysaccharide-decomposing enzyme (alginate lyase) to be used in the method of the present invention for producing the alginate oligosaccharide is an enzyme produced by a microorganism. As examples of the microorganism capable of producing the above-mentioned alginate lyase, those belonging to the genus Alteromonas may be cited and Alteromonas sp. No. 1786 strain is particularly preferable therefor.

The above-mentioned microorganism (Alteromonas sp. No. 1786 strain) is obtained from the intestines of horseshoe crabs through the screening of the intestines and the contents thereof by using sodium alginate as a carbon source. The morphological and physiological characteristics of this microorganism are listed in the following Table 1.

TABLE 1

Characteristics of the strain

| Morphological characteristics | Physiological characteristics |
|---|---|
| (1) Gram stain: (−) | (1) O—F test: oxidation type. |
| (2) Cell form: bacillus. | (2) Oxidase test: (+). |
| (3) Colony color: milky white | (3) Gelatin liquefaction: (+). |
| (4) Motility: yes. | (4) DNA digestion: (+). |
| (5) Flagellum: polar flagellum. | (5) Basophilicity: (+). |
| GC content*: 49.1 mol % | |

*The content of guanine and cytosine in the whole base composition of nucleic acids.

Based on the characteristics of this strain as given in the above [Table 1], attempts were made to identify it. As a result, it has been found out that this microorganism (the strain) belongs to the genus Alteromonas. This strain has been deposited with Fermentation Research Institute of the Agency of Industrial Science and Technology, whose address is 1-3 Higashi 1-chome, Tsukuba-shi, Ibaraki-ken, Japan under the accession number FERM P 11685.

Accordingly, the alginate lyase produced by the above-mentioned microorganism is the one obtained by incubating the strain having the characteristics as listed in the above [Table 1] by [Incubation Method] as will be given in Examples hereinafter. The enzymological properties of this alginate lyase are as follows.

(1) Action: When sodium alginate (potassium alginate) employed as a substrate is treated with the alginate lyase produced by the above-mentioned microorganism, an increase in the absorbance at 230 nm corresponding to the specific absorption wavelength assignable to the double bond in the sodium alginate oligosaccharide (potassium alginate oligosaccharide), i.e., the reaction product and an increase in the reducing power due to the oligosaccharide thus formed are observed.

(2) Optimum pH: The alginate lyase produced by the above-mentioned microorganism shows a relatively high activity within a pH range of 7.0 to 7.5. The optimum pH value is 7.0 at which the maximum relative activity is achieved.

(3) Optimum temperature and heat stability: The alginate lyase produced by the above-mentioned microorganism shows a high relative activity within a temperature range of 45° to 55° C. The optimum temperature is 50° C. at which the maximum relative activity is achieved. Regarding its heat stability, it remains stable in the form of a crude enzyme up to around 50° C. at which the maximum relative activity is observed. No decrease in the enzymatic activity is observed even when concentrated at room temperature.

When the alginate lyase produced by the above-mentioned microorganism is to be used in the method for producing the potassium alginate oligosaccharide of the present invention, the reaction with potassium alginate and/or sodium alginate is preferably effected at a temperature of 45° to 55° C., since the enzymatic activity of said alginate lyase is maintained at a high level within a temperature range of 45° to 55° C.

(4) Enzymatic activity: The enzymatic activity of alginate lyase can be measured by using a reaction mixture of the composition as specified below, reacting sodium alginate (potassium alginate) with alginate lyase at 50° C. for 10 minutes, and determining the oligosaccharide thus formed by Nelson-Somogyi's method. This enzymatic activity is expressed by taking the amount of the enzyme capable of forming sodium alginate oligosaccharide (potassium alginate oligosaccharide) corresponding to 1 μmol of mannuronic acid as 1 unit (U).

(Composition of Reaction Mixture)

0.05M sodium phosphate buffer solution (pH 7.0) containing 0.5% of sodium alginate (manufactured by Wako Pure Chemical Industries, Ltd.) . . . 0.45 ml enzyme suspension . . . 0.05 ml.

In the method for producing the alginate oligosaccharide of the present invention, alginate lyase obtained by incubating a strain, which is a mutant obtained by treating the above-mentioned strain by a conventional means for mutation and capable of producing the alginate lyase, is usable.

In the method for producing the alginate oligosaccharide of the present invention, an example of the method for eliminating potassium ion or sodium ion from (deionizing) potassium alginate oligosaccharide and/or sodium alginate oligosaccharide is the one comprising adding said oligosaccharide to a column packed with a carrier such as a strongly acidic cation exchange resin to thereby contact with said carrier and then eluting with desalted water.

In the method for producing the alginate oligosaccharide of the present invention, calcium hydroxide may be cited as an example of the hydroxide to be used in the treatment of the calcium alginate oligosaccharide with calcium after once eliminating potassium ion or sodium ion from (deionizing) the above-mentioned potassium alginate oligosaccharide and/or sodium alginate oligosaccharide. In the case of the potassium alginate oligosaccharide, on the other hand, potassium hydroxide may be cited as an example of the hydroxide of potassium.

The above-mentioned method for producing potassium alginate oligosaccharide according to the present invention makes it possible to produce a potassium-enriched potassium alginate oligosaccharide which contains little sodium. Since sodium per se is a factor relating to the elevation of blood pressure, it is an ideal method for producing potassium alginate oligosaccharide to be used as an antihypertensive drug while reducing the sodium contained therein.

The potassium alginate oligosaccharide thus obtained preferably contains 10% or more, still preferably from 10 to 20%, of potassium ion based on the total weight of the whole oligosaccharide.

The calcium alginate oligosaccharide thus obtained preferably contains 5% or more, still preferably from 5 to 15%, of calcium ion based on the total weight of the whole oligosaccharide.

Examples of the desalting/purifying method to be used in the method for producing the alginate oligosaccharide according to the present invention include gel filtration and salting out. In the case of a treatment on a small scale of several grams, for example, the above-mentioned oligosaccharide is poured into a column packed with a fractional gel filtration carrier of the oligosaccharide and then eluted with desalted water (see Japanese Patent Laid-Open No. 169188/1992).

As the above-mentioned oligosaccharide fractional gel filtration carrier, those having a fractional molecular weight ranging from 100 to 1800 daltons are preferable. As particular examples thereof, Bio-Gel P-2 and Bio-Gel P-6DG (each manufactured by Bio-Rad Laboratories) may be cited.

In the case of a treatment on a large scale of several hundred grams or above, it is preferable to use an electrodialyzer (for example, Micro Acylizer®, manufactured by Asahi Chemical Industry, Co., Ltd.).

When added to foods, the alginate oligosaccharide of the present invention exerts an antihypertensive action and thus contributes to the prevention of hypertension and the maintenance of the health. The degree of polymerization of the above-mentioned alginate oligosaccharide showing the antihypertensive action is from 2 to 5.

When the alginate oligosaccharide of the present invention is to be used in foods, it may be added to common foods such as juice, candy, chewing gum and ice cream by conventional methods in such an amount as not to deteriorate the tastes of the foods. More particularly, the content may preferably range from 1 to 10% by weight, still preferably from 2.5 to 5% by weight.

To further illustrate the alginate oligosaccharide of the present invention in greater detail, the following Examples will be given. However, it is to be noted that the technical scope of the present invention is not restricted thereto. The [Incubation Method] as specified below means a method for incubating the above-mentioned microorganism (the strain) for obtaining the alginate lyase to be used in the present invention.

| [Incubation Method] | |
|---|---|
| (Composition of medium) | |
| sodium alginate | 10 g |
| artificial seawater*[1] | 1000 ml |
| Fe stock*[2] | 1 ml |
| Pi stock*[3] | 2 ml |
| $NH_4$ stock*[4] | 5 ml |
| 1M tris-HCl buffer (pH 7.8) | 50 ml |

*[1]artificial seawater: 300 mM sodium chloride, 10 mM potassium chloride, 50 mM magnesium sulfate (heptahydrate), 10 mM calcium chloride (dehydrate).
*[2]Fe stock: 10 g of iron ammonium citrate/100 ml of desalted water.
*[3]Pi stock: 7.5 g of dipotassium hydrogenphosphate (trihydrate)/100 ml of desalted water.
*[4]$NH_4$ stock: 20 g of ammonium chloride/100 ml of desalted water.

By using a medium of the composition as specified above, a freeze-dried stock strain of Alteromonas sp. No. 1786 was preincubated twice (20° C., 1 day) and then the main incubation (25° C., 1 day) was effected. As a result, an alginate lyase culture showing an enzymatic activity of 0.84 U/ml of culture broth was obtained.

Cells were removed from the above-mentioned culture broth by using an ultrafiltration membrane of a fractional molecular weight of 500,000 (manufactured by Romicon B.V.) and thus a crude alginate lyase solution was obtained.

EXAMPLE 1

Production of potassium alginate oligosaccharide and sodium alginate oligosaccharide 439 g of potassium alginate was dissolved in 8000 ml of desalted water. Then 2350 U of the alginate lyase concentrate produced by the above-mentioned [Incubation Method] was added thereto and the mixture was allowed to react at 40° C. for 24 hours under stirring. Thus potassium alginate oligosaccharide was obtained.

The above procedure was repeated except that the potassium alginate as replaced with sodium alginate. Thus sodium alginate oligosaccharide was obtained. Further, a mixture of potassium alginate oligosaccharide and sodium alginate oligosaccharide was obtained by using a mixture of potassium alginate and sodium alginate.

EXAMPLE 2

Preparation of calcium alginate oligosaccharide

The potassium alginate oligosaccharide produced in the above Example 1 was added to a column (8 cm in diameter× 30 cm) packed with Dowex 50W (a strongly acidic cation exchange resin, manufactured by Dowex) and eluted with desalted water to thereby eliminate potassium ion.

The alginate oligosaccharide, from which potassium ion had been eliminated, was fractionated on a fraction collector and fractions of pH 2 or below and showing absorption at 230 nm were further collected.

An excessive amount of calcium hydroxide was added to these fractions and the mixture was stirred at room temperature overnight. Thus calcium alginate oligosaccharide was obtained.

The above-mentioned procedure was repeated twice. Thus 358 g of calcium alginate oligosaccharide was prepared from the potassium alginate oligosaccharide prepared in the above Example 1.

The calcium alginate oligosaccharide thus prepared was neutralized with hydrochloric acid, freeze-dried and desalted (see Example 4) or directly treated on an electrodialyzer (manufactured by Asahi Chemical Industry Co., Ltd.).

Further, the sodium alginate oligosaccharide prepared in the above Example 1 was treated by the same method as the one described above and thus calcium alginate oligosaccharide was obtained.

EXAMPLE 3

Preparation of potassium-enriched potassium alginate oligosaccharide

The potassium alginate oligosaccharide produced in the above Example 1 was added to a column (8 cm in diameter× 30 cm) packed with Dowex 50W (a strongly acidic cation exchange resin, manufactured by Dowex) and eluted with desalted water to thereby eliminate potassium ion.

The alginate oligosaccharide, from which potassium ion had been eliminated, was fractionated on a fraction collector and fractions of pH 2 or below and showing absorption at 230 nm were further collected.

An excessive amount of potassium hydroxide was added to these fractions and the mixture was stirred at room temperature overnight. Thus potassium alginate oligosaccharide was obtained.

Thus 510 g of potassium-enriched potassium alginate oligosaccharide was prepared from 1,000 g of the potassium alginate oligosaccharide prepared in the above Example 1.

The potassium alginate oligosaccharide thus prepared was neutralized with hydrochloric acid, freeze-dried and desalted (see Example 4) or directly treated on an electrodialyzer (manufactured by Asahi Chemical Industry Co., Ltd.) to thereby eliminate the excessive potassium hydroxide and purified.

Further, the sodium alginate oligosaccharide prepared in the above Example 1 was treated by the same method as the one described above and thus potassium alginate oligosaccharide was obtained.

EXAMPLE 4

Purification of calcium alginate oligosaccharide

About 20 g of the calcium alginate oligosaccharide prepared in the above Example 2 was desalted by adding to a column (15 in diameter×30 cm) packed with Bio-Gel P-6DG (a gel filtration carrier, manufactured by Bio-Rad Laboratories) and then eluting with desalted water. The calcium alginate oligosaccharide thus desalted was fractionated on a fraction collector and fractions of an electric conductance of 1 m.mho or below and showing absorption at 230 nm were collected and freeze-dried. By using this column, about 10 g of calcium alginate oligosaccharide could be isolated and purified.

The above procedure was repeated to thereby isolate and purify calcium alginate oligosaccharide prepared from sodium alginate oligosaccharide in the above Example 2.

The following [Table 2] shows the results of an elemental analysis of the calcium alginate oligosaccharide thus prepared, though the data of the above-mentioned elemental analysis are not restricted thereto.

TABLE 2

| Elemental analysis of calcium alginate oligosaccharide | | | |
|---|---|---|---|
| Starting material | Ca | K | Na |
| potassium alginate | 8.7% | 0.8% | 0.4% |
| sodium alginate | 4.9% | 0.7% | 1.4% |

Regarding the potassium alginate oligosaccharide of the above Example 3, the oligosaccharide obtained simply by treating potassium alginate with the enzyme was compared with another oligosaccharide obtained by decomposing with the enzyme, deionizing and adding the potassium ion again on the level of elemental analysis. The following [Table 3] shows the results. As Table 3 indicates, the oligosaccharide obtained by deionizing and treating with the potassium salt again showed an elevated potassium content.

TABLE 3

| Elemental analysis of potassium alginate oligosaccharide | | |
|---|---|---|
|  | K | Na |
| treating an alginate oligosaccharide with the enzyme | 5.1% | 4.5% |
| treating potassium alginate with the enzyme, deionizing and adding the potassium. | 12.1% | 1.2% |

EXAMPLE 5

Test on antihypertensive action I

Spontaneous hypertensive rats (SHR), each group consisting of 6 animals, were fed with feeds of the compositions as specified below continuously for 4 weeks.

Specifically, a calcium alginate oligosaccharide group was fed with a powdery formulated feed MF [manufactured by Oriental Yeast Co., Ltd.] to which 2.5% of calcium alginate oligosaccharide and 1% of NaCl were added. On the other hand, a control group was fed with a powdery formulated feed MF [manufactured by Oriental Yeast Co., Ltd.] to which 1% of NaCl was added.

After starting the test, the blood pressure of each SHR was measured at intervals of 1 week with the use of a bloodless tail artery meter [manufactured by Riken Kaihatsu K.K.].

FIG. 1 shows the results. As FIG. 1 clearly indicates, the increase in the average blood pressure of the group fed with calcium alginate oligosaccharide was remarkably suppressed in the third week following the initiation of the test, compared with the control group, thus showing an antihypertensive action.

EXAMPLE 6

Test on antihypertensive action II

Spontaneous hypertensive rats (SHR), each group consisting of 6 animals, were fed with feeds of the compositions as specified below continuously for 5 weeks.

Specifically, a potassium alginate oligosaccharide group was fed with a powdery formulated feed MF [manufactured by Oriental Yeast Co., Ltd.] to which 2.5% of potassium alginate oligosaccharide and 1% of NaCl were added. On the other hand, a control group was fed with a powdery formulated feed MF [manufactured by Oriental Yeast Co., Ltd.] to which 1% of NaCl was added.

After starting the test, the blood pressure of each SHR was measured at intervals of 1 week with the use of a bloodless tail artery meter [manufactured by Riken Kaihatsu K.K.].

Figure 2:
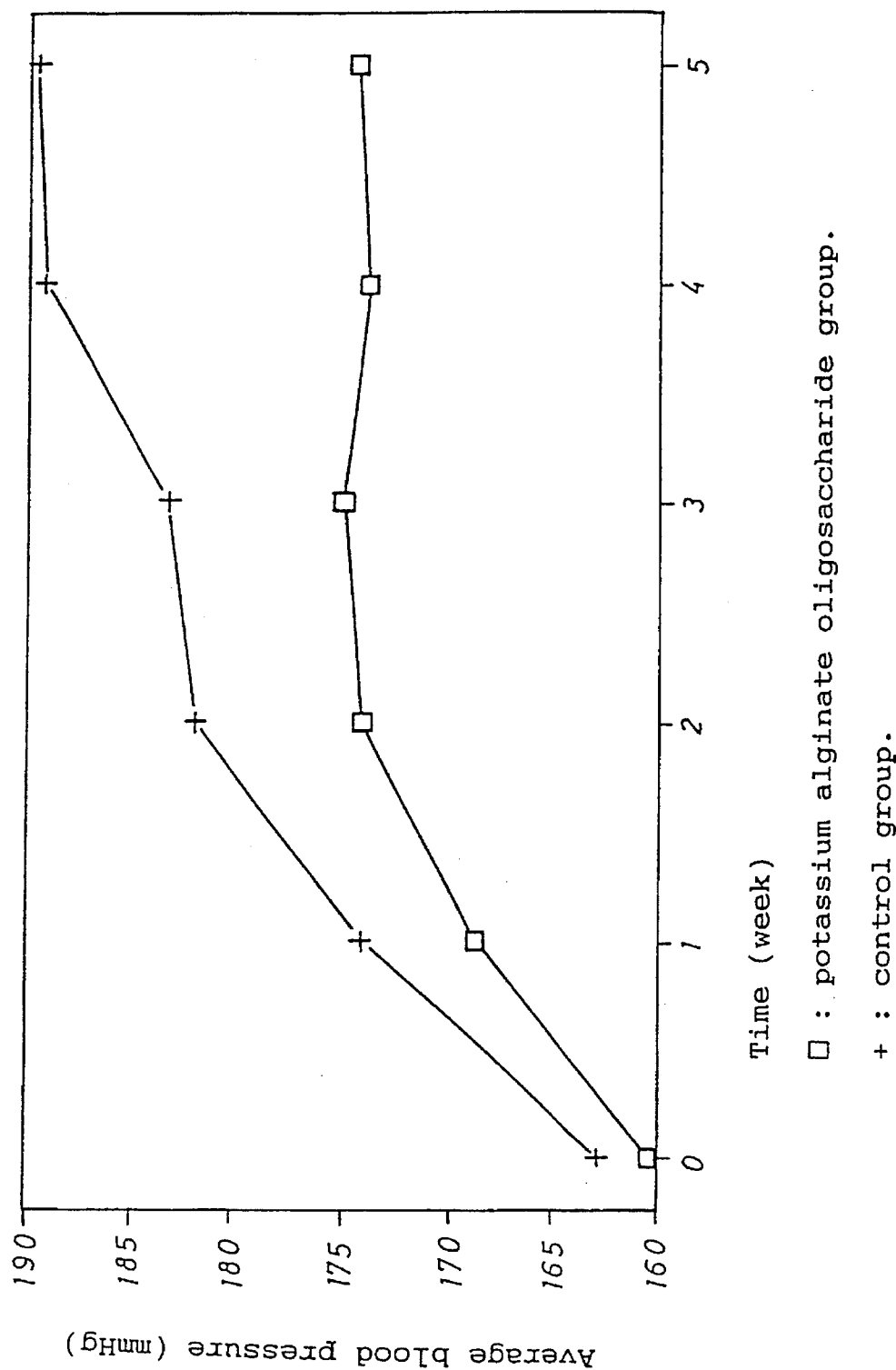
FIG. 2 is a graph showing the antihypertensive action of the potassium alginate oligosaccharide according to the present invention in an antihypertensive test described in Example 6 as will be given hereinafter wherein SHRs were used.

FIG. 2 shows the results. As FIG. 2 clearly indicates, the increase in the average blood pressure of the group fed with potassium alginate oligosaccharide was remarkably suppressed in the second week following the initiation of the test, compared with the control group, thus showing an antihypertensive action.

The following Examples will show examples for production of foods.

EXAMPLE 7

Production of juice containing calcium alginate oligosaccharide or potassium-enriched potassium alginate oligosaccharide (hereinafter referred to as alginate oligosaccharide)

A juice of the following composition was produced.

| Juice (1000 ml in total) | |
|---|---|
| alginate oligosaccharide | 25 g |
| liquid sugar | 80 ml |
| honey | 10 ml |
| wine | 10 ml |
| perfume | 2 ml |
| vitamin C | 2 ml |
| water | 896 ml. |

EXAMPLE 8

Production of candy containing alginate oligosaccharide
A candy of the following composition was produced.

| Candy (100 g in total) | |
|---|---|
| alginate oligosaccharide | 2.5 g |
| sugar | 37.5 g |
| starch syrup | 60.0 g. |

EXAMPLE 9

Production of chewing gum containing alginate oligosaccharide
A chewing gum of the following composition was produced.

| Chewing gum (100 g in total) | |
|---|---|
| alginate oligosaccharide | 2.5 g |
| gum base | 37.5 g |
| sugar | 43.0 g |
| glucose | 10.0 g |
| corn syrup | 5.0 g |
| perfume | 2.0 g. |

EXAMPLE 10

Production of ice cream containing alginate oligosaccharide
An ice cream of the following composition was produced.

| Ice cream (100 g in total) | |
|---|---|
| alginate oligosaccharide | 2.5 g |
| defatted milk powder | 8.0 g |
| vegetable fat | 10.0 g |
| sugar | 13.0 g |
| stabilizer | 0.3 g |
| emulsifier | 0.3 g |
| vanilla flavor | 0.1 g |
| yolk | 7.5 g |
| water | 58.3 g. |

EXAMPLE 11

In this Example, an example of the analysis on the degree of polymerization of the calcium alginate oligosaccharide of the present invention will be described.

The degree of polymerization was determined by thin layer chromatography (TLC).

First, a standard substance was prepared by hydrolyzing sodium alginate with 1N trifluoroacetic acid at 100° C. for 24 hours. Alternately, potassium alginate may be used as a standard substance.

TLC was effected under the following conditions.

Thin layer plate: a silica gel 60 HPTLC plate (manufactured by Merck & Co., Inc.).

Developing solvent: 1-butanol/acetic acid/water (5/2/3).

Coloring reagent: a diphenylamine-aniline-phosphoric acid reagent.

Figure 3:
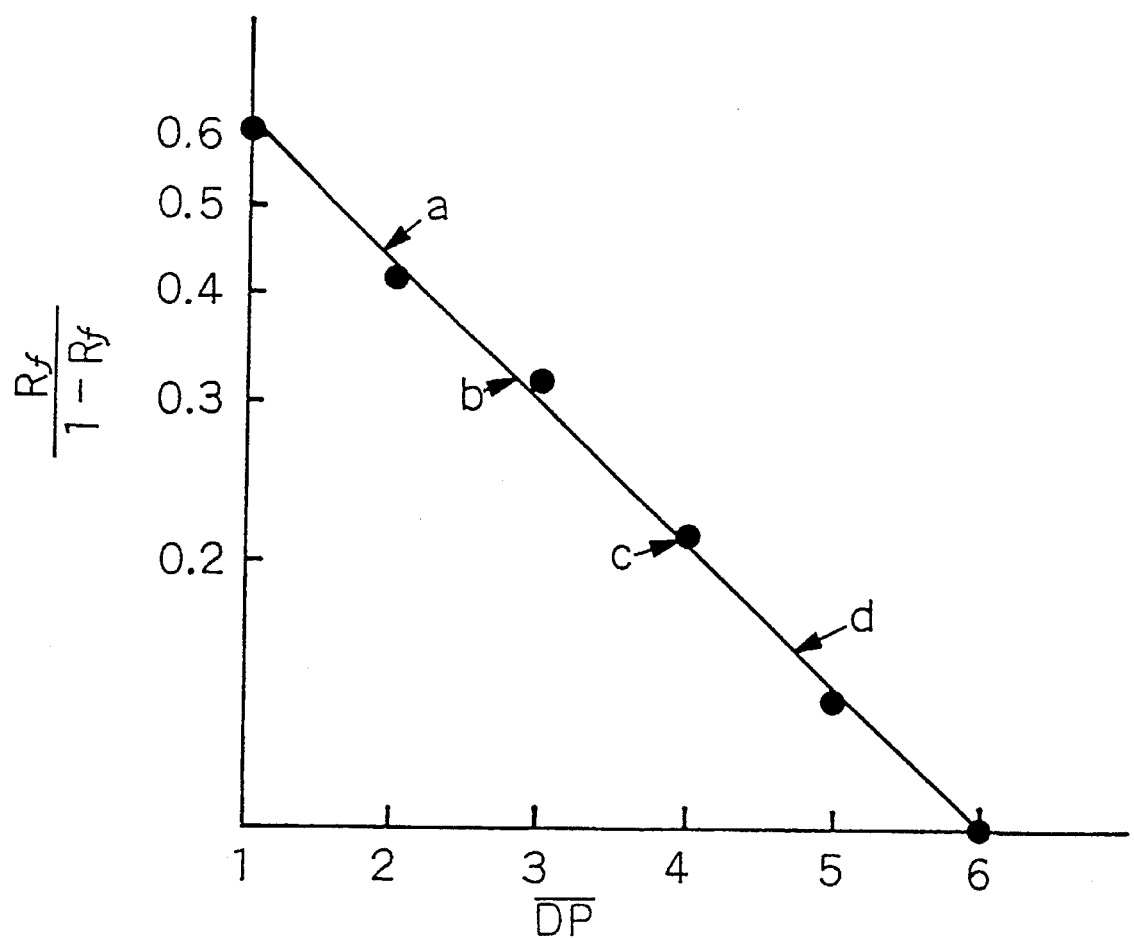
FIG. 3 gives a calibration line showing the relationship between the degree of polymerization of each oligosaccharide such as sodium alginate oligosaccharide and the relative mobility thereof in thin layer chromatography.

The above-mentioned sodium alginate hydrolyzate (the standard substance) was subjected to TLC. As a result, six spots were obtained. Among these six spots, one showing the largest mobility agreed with that of D-mannuronic acid [obtained by treating D-mannuronic acid lactone (manufactured by Sigma) with an alkali to thereby remove the lactone ring; Rf value: 1.00, DP=1]. Further, spots showing Rf values of 0.74 and 0.69 were subjected to gel filtration with the use of Bio-Gel P-2 [1.5×46 cm, eluted with 0.1M acetate buffer solution (pH 4.0)] to thereby give purified oligosaccharides. The uronic acid content and the reducing sugar content in these purified oligosaccharides were determined respectively by the orcinoliron hydrochloride method [see Brown; Arch. Biochem., 11, 269–278 (1946)] and Somogyi-Nelson's method [see Somogyi; J. Biol. Chem., 195, 19–23 (1952), Nelson; J. Biol. Chem., 153, 375–380 (1944)] and the degrees of polymerization (DP) were calculated based on the ratio of uronic acid to reducing sugar. As a result, the degrees of polymerization of these spots were respectively 1.93 and 3.04. Then the relationship between relative mobility (Rf/1-Rf) and degree of polymerization (DP) was plotted by using these two purified oligosaccharides, D-mannuronic acid and other three spots and a calibration line was formed. As a result, these six spots showed a linearity. FIG. 3 shows this calibration line.

Figure 4A:
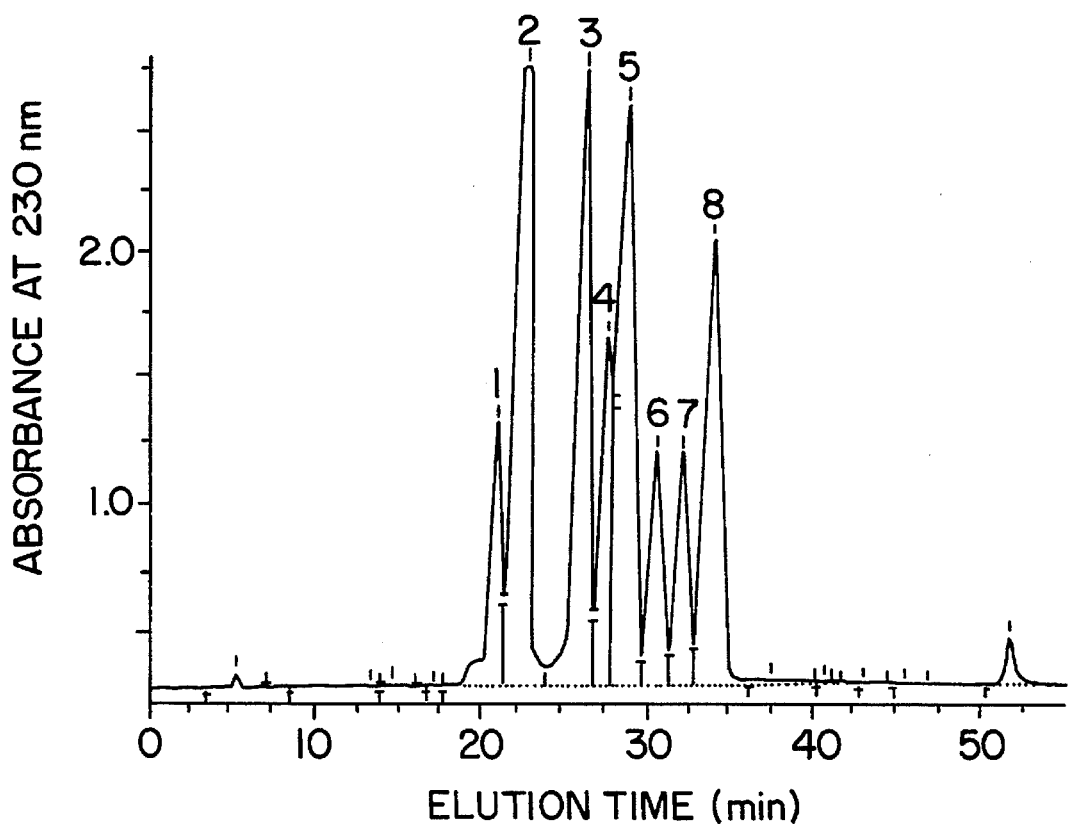
Figure 4B:
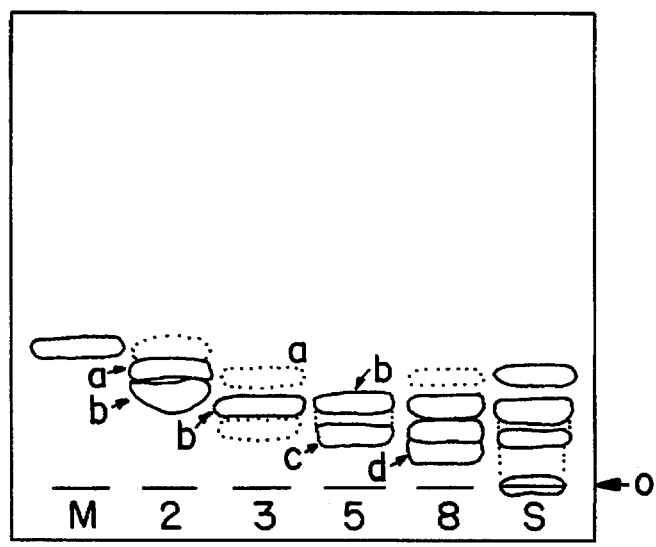
FIG. 4(b) is a thin layer chromatogram of sodium alginate oligosaccharide.

Next, the sodium alginate oligosaccharide prepared by the method described in the above Example 1 was subjected to high performance liquid chromatography under 0–2M gradient elution of NaCl with the use of DEAE Glass (manufactured by Nacalai Tesque, Inc.) and then fractionated on a fraction collector (see Japanese Patent Laid-Open No. 266896/1992). FIG. 3(a) shows the elution pattern thus obtained. From among fractions F-1 to P-8 showing absorption at 230 nm, the major ones (P-2, P-3, P-5 and P-8) were collected. Each of these fractions was desalted (see Japanese Patent Laid-Open No. 169188/1992) by using a column packed with Bio-Gel P-2 (manufactured by Bio-Rad Laboratories), freeze-dried and then subjected to TLC. Thus a thin layer chromatogram as shown in FIG. 4(b) was obtained. In FIG. 4(b), 0 represents the starting point, M represents D-mannuronic acid, S represents an oligosaccharide obtained by the enzymatic decomposition of sodium alginate, 2 represents the fraction P-2, 3 represents the fraction P-3, 5 represents the fraction P-5 and 8 represents the fraction P-8. Further, a, b, c and d represents each a spot of a calculated Rf value.

As the thin layer chromatogram of FIG. 4(b) shows, none of the samples gave a single spot. Then the Rf values of main spots were determined and plotted on the calibration line given in FIG. 3 to thereby examine the degree of polymerization. As a result, it was proved that the degrees of polymerization of the fractionated oligosaccharides (P-2, P-3, P-5 and P-8) ranged mainly from 2 to 5.

Thus the sodium alginate oligosaccharide is a mixture with a degree of polymerization of 2 to 5. It was assumed that the degree of polymerization of the potassium alginate oligosaccharide, which was obtained by once eliminating sodium ion or potassium ion in sodium alginate oligosaccharide or potassium alginate oligosaccharide and then substituting with potassium ion, might be a mixture with a degree of polymerization of 2 to 5, too.

Figure 5:
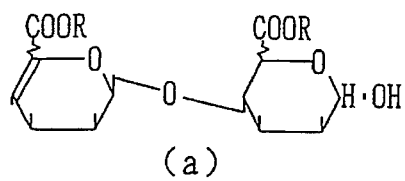
FIG. 5 is a schematic view of the structures of calcium alginate oligosaccharide, sodium alginate oligosaccharide and potassium alginate oligosaccharide.
Figure 5:
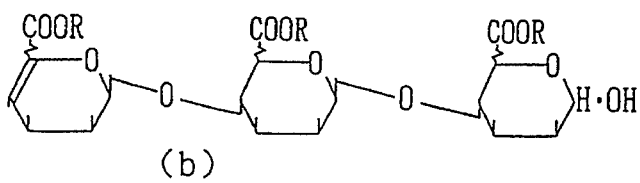
Figure 5:
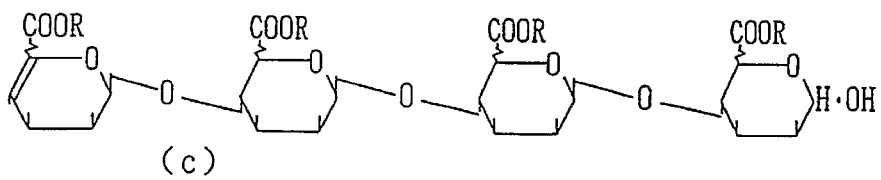
Figure 5:
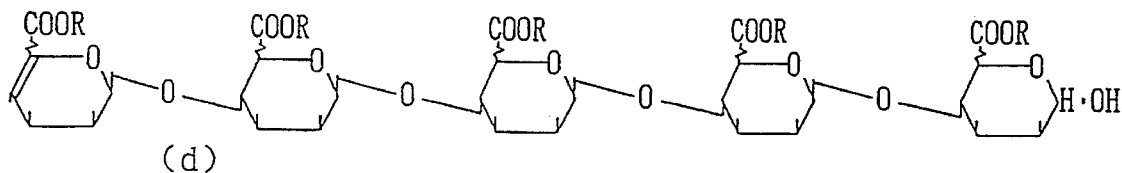
Figure 5:
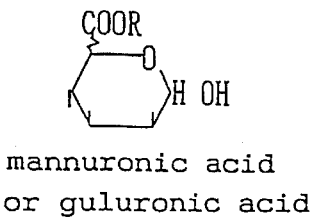
Figure 5:
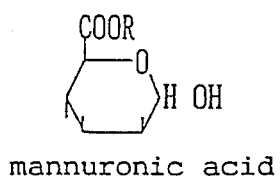
Figure 5:
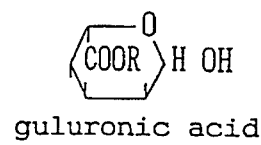

FIG. 5 is a schematic view of the structures of calcium alginate oligosaccharide, sodium alginate oligosaccharide and potassium alginate oligosaccharide according to the present invention. Structure (a) shows an oligosaccharide having a degree of polymerization of 2, structure (b) shows one having a degree of polymerization of 3, structure (c) shows one having a degree of a polymerization of 4 and structure (d) shows one having a degree of polymerization of 5. The constituting sugars of these oligosaccharides are D-mannuronic acid and L-guluronic acid which may be any of the homo and hetero types. R in the COOR group is one selected from among H, Na, K and Ca.

Accordingly, the alginate oligosaccharide of the present invention contributes to the maintenance of the health by, for example, preventing hypertension.

What is claimed is:

1. A calcium alginate oligosaccharide obtained by
   (a) treating potassium alginate and/or sodium alginate with an alginate lyase produced by a microorganism to obtain a potassium alginate oligosaccharide and/or sodium alginate oligosaccharide having a degree of polymerization from 2 to 5; and
   (b) substituting the potassium ion or sodium ion in the potassium alginate oligosaccharide and/or sodium alginate oligosaccharide with calcium ion.

2. The calcium alginate oligosaccharide as claimed in claim 1, wherein said microorganism belongs to the genus Alteromonas.

3. The calcium alginate oligosaccharide as claimed in claim 2, wherein said microorganism is Alteromonas sp. No. 1786 strain FERM P-11685.

4. An antihypertensive food containing the alginate oligosaccharide as claimed in claim 1.

* * * * *